US008036925B2

(12) United States Patent
Choubey

(10) Patent No.: US 8,036,925 B2
(45) Date of Patent: Oct. 11, 2011

(54) SYSTEM AND METHOD TO MANAGE ASSETS OF HEALTHCARE FACILITY

(75) Inventor: Suresh Choubey, Delafield, WI (US)

(73) Assignee: General Electric Company, Schenectady, NY (US)

( * ) Notice: Subject to any disclaimer, the term of this patent is extended or adjusted under 35 U.S.C. 154(b) by 411 days.

(21) Appl. No.: 12/013,808

(22) Filed: Jan. 14, 2008

(65) Prior Publication Data

US 2009/0182594 A1 Jul. 16, 2009

(51) Int. Cl.
*G06F 17/00* (2006.01)
(52) U.S. Cl. ...................................................... 705/7.12
(58) Field of Classification Search ................ 705/7
See application file for complete search history.

(56) References Cited

U.S. PATENT DOCUMENTS

| | | | |
|---|---|---|---|
| 6,430,536 B2 * | 8/2002 | Irving et al. ...................... 705/2 |
| 6,700,493 B1 * | 3/2004 | Robinson ...................... 340/573.1 |
| 6,954,148 B2 | 10/2005 | Pulkkinen et al. |
| 2003/0074251 A1 * | 4/2003 | Kumar et al. ...................... 705/10 |
| 2006/0031095 A1 * | 2/2006 | Barth et al. ...................... 705/2 |
| 2007/0282476 A1 | 12/2007 | Song et al. |

OTHER PUBLICATIONS

Harrigan, Kathryn Rudie; An Application of Clustering for Strategic Group Analysis; Jan.-Mar. 1985; Wiley-Blackwell; Strategic Management Journal, vol. 6, No. 1; pp. 55-73.*

Mun, K., et al.; Active RFID System Augmented With 2D Barcode for Asset Management in a Hospital Setting; Mar. 26-28, 2007; 2007 IEEE INternational Conference on RFID; pp. 205-211.*

* cited by examiner

*Primary Examiner* — Susanna M Meinecke Diaz
*Assistant Examiner* — Ashley Chou
(74) *Attorney, Agent, or Firm* — Fletcher Yoder P.C.

(57) ABSTRACT

A system to manage utilization of a plurality of types of assets by a plurality of independent entities is provided. The system comprises a controller including a processor operable to execute a plurality of program instructions generally representative of the steps of receiving a plurality of parameters from each of the plurality of independent entities; segmenting the plurality the independent entities into more than one cluster dependent on identified similarities in at least one of the plurality of parameters of the one or more of the plurality of entities; and generating a display of a comparison of the plurality of parameters of each of the independent entities relative to another in each of the plurality of clusters.

18 Claims, 7 Drawing Sheets

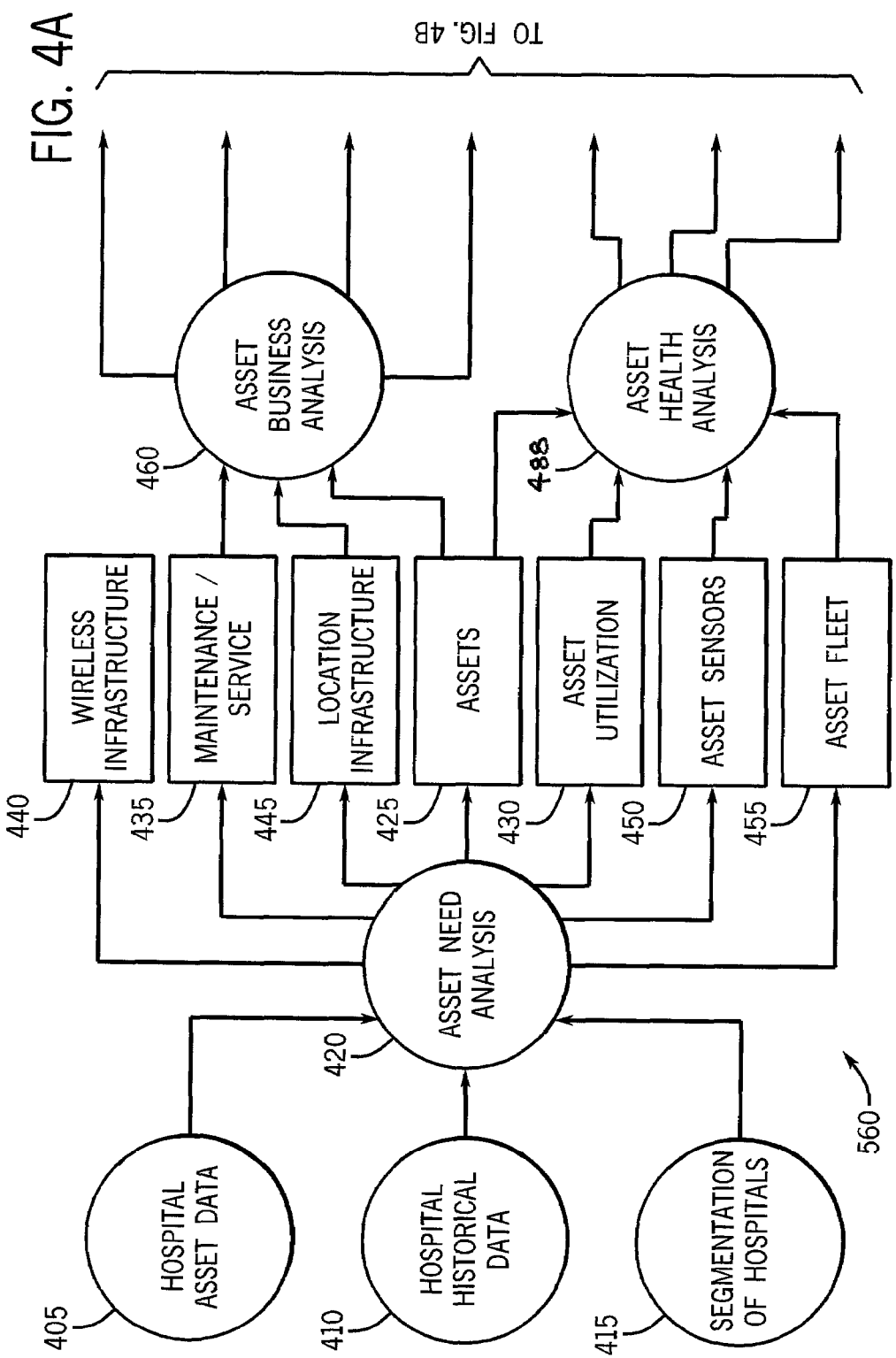

SYSTEM AND METHOD TO MANAGE ASSETS OF HEALTHCARE FACILITY

BACKGROUND OF THE INVENTION

This invention generally relates to a system for and method of managing purchases, and more particularly, to a system and method to predict or forecast needs to purchase or rent assets to track and limit movement of the at least one asset.

Larger industrial, healthcare or commercial facilities can be spread out over a large campus and include multiple floors each having multiple rooms. Each of the facilities can employ various assets used in manufacturing or providing services. For example, a healthcare facility or hospital employs numerous assets that can be spread out over a large campus and/or moved from room to room. Examples of assets include intravenous pumps, wheel chairs, digital thermometers, local patient monitors, etc. A similar scenario can be said for an industrial facility that includes various portable pumps, hoists, winches, etc.

Facilities typically acquire or purchase assets on a purely speculative basis. There is a need for a system to improve efficiency in the purchase of assets on a per department basis that does not rely on mere speculation. There is also a need for a system that includes architecture to manage assets from a prediction of need phase to a retirement or disposal phase of the asset.

BRIEF DESCRIPTION OF THE INVENTION

There is a need for a system and method to accurately locate assets in one or more hospital facilities, to increase efficiency of utilization of the assets, to accurately forecast or predict a need of assets, and to manage a life cycle of the assets. The system and method should be able to track medical devices and equipment, as well as personnel productivity and utilization. There is also a need for a system and method to increase a return on investment of purchased assets and/or service (e.g., physicians, clinicians, technicians, diagnostic equipment, laboratory equipment, etc.). There is also a need for a system and method to be able to manage the assets from a need forecast phase to a retirement of the assets. The system and method should be operable to predict and report a need of the assets, the quantity, the time of acquisition and/or rental of the assets, enhance usage of the assets, an optimal cost of operation of the assets, a maintenance of the assets, a tracking of compliance of the proper utilization of assets, tracking prediction of failure of the assets and a predicted time to fail, and a retirement and/or disposal of the assets at a local level or at an enterprise level relative to a series of entities or facilities at different remote locations or ownership.

The above-mentioned shortcomings, needs, disadvantages or problems are addressed by the embodiments described herein in the following description. According to one embodiment, a method to manage utilization of a plurality of types of assets by a plurality of independent entities is provided. The method comprises the steps of receiving a plurality of parameters from each of the plurality of independent entities; segmenting the plurality the independent entities into more than one cluster dependent on identified similarities in at least one of the plurality of parameters of the one or more of the plurality of entities; and generating a display of a comparison of the plurality of parameters of each of the independent entities relative to another in each of the plurality of clusters.

According to another embodiment, a system to manage utilization of a plurality of types of assets by a plurality of independent entities is provided. The system comprises a controller including a processor operable to execute a plurality of program instructions stored in a memory. The plurality of program instructions generally representative of the steps of receiving a plurality of parameters from each of the plurality of independent entities; segmenting the plurality the independent entities into more than one cluster dependent on identified similarities in at least one of the plurality of parameters of the one or more of the plurality of entities; and generating a display of a comparison of the plurality of parameters of each of the independent entities relative to another in each of the plurality of clusters.

Systems and methods of varying scope are described herein. In addition to the aspects and advantages described in this summary, further aspects and advantages will become apparent by reference to the drawings and with reference to the detailed description that follows.

BRIEF DESCRIPTION OF THE DRAWINGS

FIGS. 4A and 4B illustrate a schematic diagram of an architecture or framework to manage the assets of a healthcare entity from procurement/acquisition to retirement/disposal.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
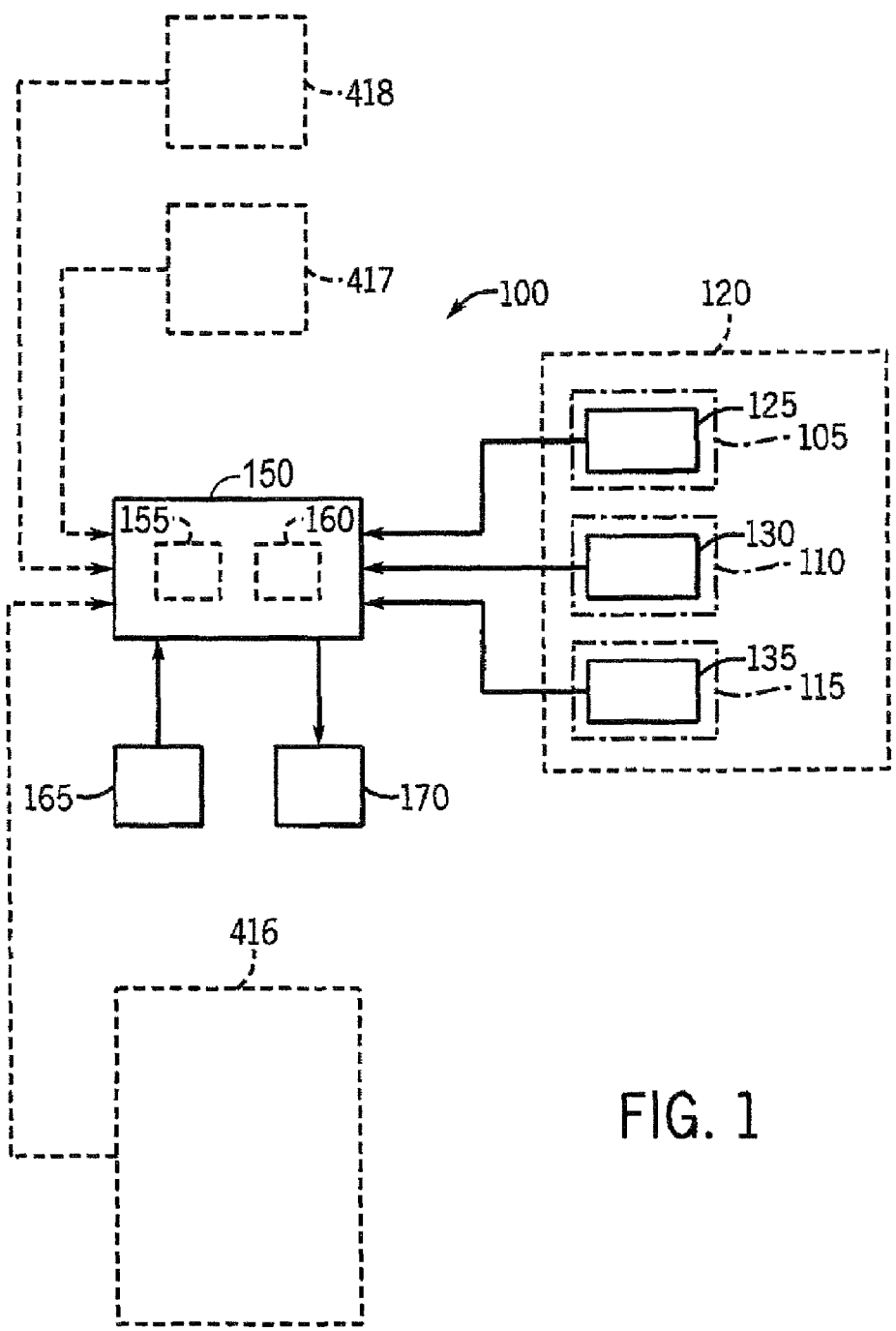
FIG. 1 shows a schematic block diagram of an embodiment of a system to manage assets of a healthcare facility.

FIG. 1 illustrates one embodiment of a system 100 to manage a series of assets 105, 110 and 115 at an entity 120 (e.g., facility, hospital, clinic, address, owner, etc.). The embodiment of the system 100 is generally operable to track movement of or locate the assets 105, 110, 115 at the entity 120, to forecast or predict a need or utilization of the assets 105, 110, 115, and to manage a life cycle of the assets 105, 110, 115.

An embodiment of the series of assets 105, 110 and 115 can include medical devices or systems which have value, and which are affiliated with the patient experience at a hospital, clinic, or other type of healthcare facility. An embodiment of the first asset 105 can be an intravenous pump, the second asset 110 can be a wheelchair, and the third asset 115 can be a healthcare personnel (e.g., physician, nurse, clinician, lab technician, etc.). The assets 105, 110, and 115 can be stationary or mobile. It should be understood that reference to the assets 105, 110, 115 can also represent individual items or devices or systems, or alternatively can represent types or fleets or similar classifications of individual devices, items or systems thereof. The number and types of assets 105, 110 and 115 can vary. Although the following description is in reference to assets 105, 110 and 115 associated with a hospital or healthcare facility, it should be understood that the subject matter is not so limited. The assets 105, 110 and 115 can be associated with various industrial or commercial environments or facilities.

The system 100 includes a series of tracking elements 125, 130, and 135 located for each asset 105, 110 and 115, respectively. The tracking elements 125, 130, and 135 are generally operable to create a signal indicative of a location or state of the respective assets 105, 110 and 115. Examples of the tracking elements 125, 130, and 135 can include a geographic positioning system (GPS) receiver in communication with a satellite, electromagnetic receivers and transmitters, radio frequency identification (RFID) tags, radio frequency (RF) transmitters/receivers, or the like or combination thereof operable to locate an absolute or relative position (e.g., a room location at a facility, a geographic location having a latitude and longitude, a coordinate, etc.) of the respective assets 105, 110, and 115 relative to a reference. The type of technique of tracking can vary.

The system 100 further includes a controller 150 in wired (e.g., communication bus) or wireless (e.g., infrared, radio frequency (RF), etc.) communication with the tracking elements 125, 130, and 135 so as to track movement of the assets 105, 110 and 115 between various states or locations. The controller 150 can also be in direct or indirect communication with one or more assets 105, 110, 115 too. Communication can be direct, or over an Internet or Ethernet or local area network (LAN) communications. An embodiment of the controller 150 can include a computer in a desktop configuration or laptop configuration. Yet, the type of controller 150 can vary.

The controller 150 generally includes one or more processors 155 in communication with a memory 160 having a computer-readable storage medium (e.g., compact disc (CD), dvd, memory stick, random access memory (RAM), random operating memory (ROM), etc.). The storage medium is generally operable to receive and record a plurality of programmable instructions for execution by the processor 155.

An embodiment of the controller 150 is also connected in communication with an input device 165 and an output device 170. The input device 165 can include one or combination of a keyboard, touch-screen, remote computer workstation, mouse, joystick, tracker ball, etc. or the like operable to receive data from an operator. The output device 170 can include a display comprising one or combination of a monitor, an alarm, light emitting diodes (LEDs), printer, audible speaker, pager, cellular phone, personal data assistant (PDA), etc. operable to visually or audibly show an output of the controller 150 for illustration to an operator. The controller 150 can also be connected in communication with a remote computer or workstation (not shown).

Figure 2:
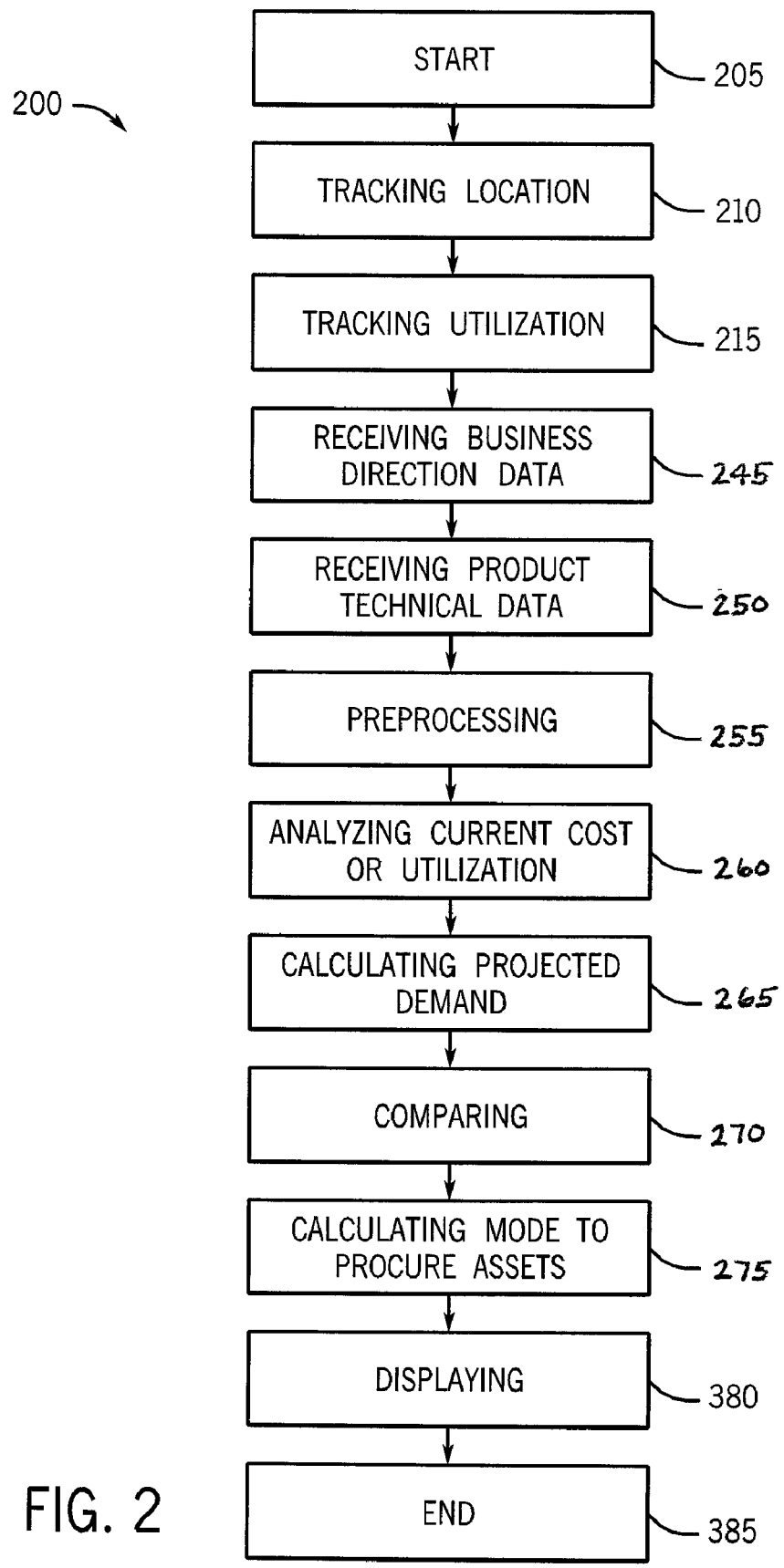
FIG. 2 illustrates an embodiment of a method to measure utilization of and generate a mode of procurement of the assets of FIG. 1.

Having described a general construction of one embodiment of the system 100, the following is a general description of an embodiment of a method 200 to procure one or more assets 105, 110, 115 at the entity 120 as illustrated in FIG. 2. It should also be understood that the sequence of the acts or steps of the method 200 as discussed in the foregoing description can vary. Also, it should be understood that the method 200 may not require each act or step in the foregoing description, or may include additional acts or steps not disclosed herein. An embodiment of the steps or acts of the method 200 in the foregoing description can be represented as programming instructions for execution by the processor 155 of the controller 150 or stored on the memory 160 (e.g., dvd, cd, hard-drive, etc.).

FIG. 2 illustrates one embodiment of the method 200. Act 205 includes the start of the method 200. Act 210 includes tracking a location of each asset 105, 110, and 115. An embodiment of act 210 includes receiving a signal via the tracking element 125, 130, and 135 representative of a location data of each asset 105, 110, and 115 in combination with a unique identifier of the asset 105, 110, and 115 on a periodic or continuous basis. Act 210 can further include receiving a status or health (e.g., in need of repair, in need of maintenance, etc.) of the asset 105, 110, and 115.

Act 215 includes tracking or measuring utilization of each asset 105, 110, and 115 or type thereof and communicating the measurement data to the controller 150. An embodiment of act 215 includes calculating a utilization of assets of each type or category of assets (e.g., fleet of intravenous pumps, fleet of wheelchairs, etc.) and on an individual asset basis (e.g., wheelchair No. 1, wheelchair No. 2, etc.). Utilization can be measured by incremental time periods (e.g., minutes, hours, days, etc.) that each asset 105, 110, and 115 spends or dwells or is identified at a particular status indicator or state of use/utilization. An embodiment of calculating utilization includes calculating or measuring the period of time that the asset 105, 110, and 115 spent or dwelled in a recognized state of use/utilization. For example, the act of calculating utilization can include calculating a percentage of actual demand or utilization of the at least one asset 105, 110 and 115 over a time interval.

Figure 3:
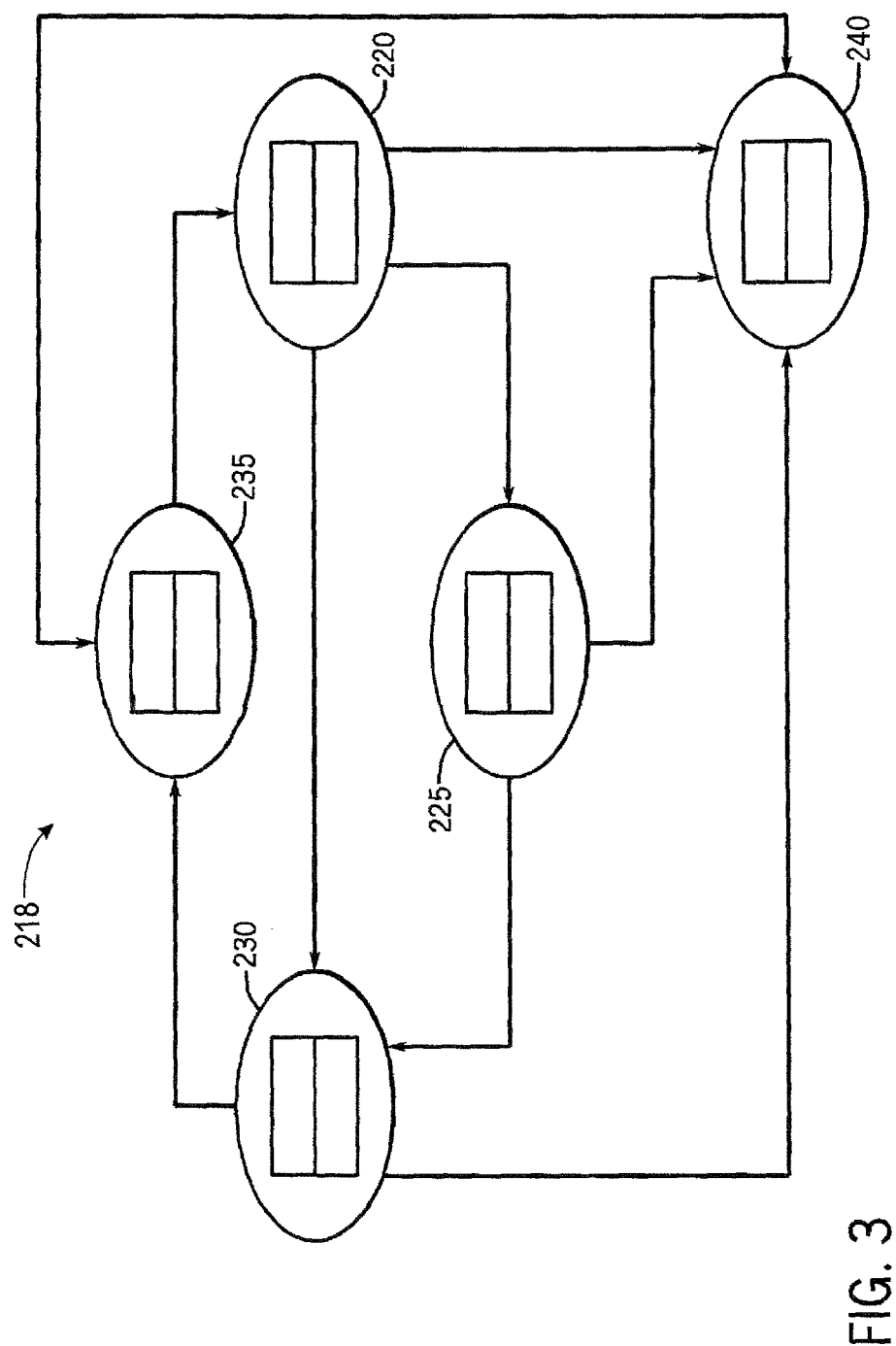
FIG. 3 illustrates a schematic diagram of an embodiment of tracking a change of state of one or more assets of FIG. 1.

In one example, the utilization status is communicated with location data for the asset 105, 110, and 115. In another example, the acquired data for the utilization status can be equated to the acquired location data of the asset 105, 110, and 115. Predetermined status identifiers or index of utilization can be stored in correlation or equated to various locations of the assets 105, 110, and 115. A status indicator can be "not in use" if a location of one of the assets 105, 110, and 115 is in a storage room, a dirty room, a cleaning room, or a service room while a status indicator can be "in use" if the location of the asset 105, 110, and 115 is in a patient room. An embodiment of act 215 includes communicating the tracked use for illustration at the output device 170. FIG. 3 shows an example of a graphic illustration 218 of the tracked used for illustration at the output device 170.

Examples of calculating utilization of the assets 105, 110, and 115 include calculating daily asset utilization that is generally equal to a sum (in hours/day) of utilization or use of each type of asset 105, 110, and 115 divided by number of a type of assets 105, 110, and 115; calculating a weekly asset utilization that is generally equal to a sum of daily asset utilization for a calendar week for each type of asset 105, 110, and 115 divided by sevens day/week; calculating a monthly asset utilization that is generally equal to sum of daily asset utilization of each type of asset 105, 110, and 115 for a calendar month divided by number of days in calendar month; and calculating a yearly asset utilization that is generally equal to sum of daily asset utilization for calendar year for each type of asset 105, 110, and 115 divided by number of days in a calendar year. Act 215 can further include normalizing the utilization of the assets 105, 110, and 115 according to a number of effective operational hours in a day at the entity (e.g., entity is only open to the public for twelve hours per day).

Referring to FIG. 3, one embodiment of the various states or status indicators of each asset 105, 110, and 115 at any given time as tracked in act 215 includes a USE status or state 220, a DIRTY state 225, a CLEANING state 230, an INVENTORY state 235, and a SERVICE state 240 of each of the assets 105, 110, and 115. The USE state 220 represents the assets 105, 110, and 115 being utilized by a patient or subject either in a patient room or with the patient transitioning from one point or location to another (e.g., for a walk, to get testing, etc.). The DIRTY state 225 represents the assets 105, 110, and 115 being temporarily stored before being taken to a location of a CLEANING state 230 or, if malfunctioning, to the SERVICE state 240. The CLEANING state 230 represents status of the assets 105, 110, and 115 in the process of being cleaned of contamination or under routine maintenance or in a service/maintenance room such that not currently available, but so as to be available at a future time for utilization according to the USE state 220. The INVENTORY state 235 represents status of the assets 105, 110, and 115 that have previously been moved from the CLEANING state 230 and are now in storage and ready for use in accordance with the USE state 220 described above. The SERVICE state 240 represents status of the assets 105, 110, and 115 after malfunctioning or requiring repair or to be discarded. It should be understood that the types and number of state or statuses to describe the type of tracked utilization (and duration thereof) of the assets 105, 110, 115 can vary.

A technical effect of measuring the dwell time of the assets 105, 110, 115 in the CLEANING state 230 or the SERVICE state 240 or the DIRTY state 225 and a number of personnel correlated with those assets 105, 110, 115 while in each of the above-described respective states 225, 230, 240 are factors to calculate a replacement or procurement of the respective assets 105, 110, 115, or factors to calculate a schedule of trips to the respective location (e.g., service room) to retrieve the assets 105, 110, 115 when ready for utilization.

An embodiment of measuring dwell time in the INVENTORY state 235 can be directly dependent or correlated to a quantity of the assets 105, 110, 115 or fleet thereof in the INVENTORY state 235. The tracked or measure of dwell time in the INVENTORY state 235 can be a factor to calculate a prediction of a future demand or procurement of the assets 105, 110, 115.

An embodiment of act 215 can include tracking the status indicator of one or more of the assets 105, 110, and 115 having the unique identifier on a continuous or periodic basis. In one example, the status is communicated with location data for the asset 105, 110, and 115 from the respective tracking elements 125, 130, and 135. In another example, the status indicator can be automatically assigned in accordance to a predetermined schedule correlating each of the series of status indicators to one or more possible detected or tracked locations of each of the assets 105, 110, and 115. For example, a status indicator can be automatically assigned to the unique identifier of the asset to be in the USE state if the location of the asset 105, 110, and 115 is detected to be in a patient room or location correlated according to a predetermined schedule to the USE state. Alternatively, the status indicator can be manually entered at the input 165 to the controller 150 for each asset 105, 110, and 115.

Referring to FIG. 3, act 245 includes receiving data of predictive parameters associated with a future business plan or direction correlated with a predicted change in utilization of one or more of the assets 105, 110, and 115 looking forward in time. Examples of a predicted business direction change in utilization of the assets includes identifying a first factor representative of a predicted increase or decrease in services associated with utilization of the assets, identifying a second factor representative of a predicted change in demand for utilization of the assets associated with a change in competition or government regulations or in view of an expected creation of a new department.

Act 250 includes receiving data of designated technical parameters associated with each asset or type thereof. Examples of technical parameters include expected date of retirement or disposal (e.g., expected useful life), efficiency, purchase cost to replace, rental or lease cost, dates and list of routine maintenance items, expected release date of new model or evolving technology, etc.

Act 255 includes integrating, cleaning, and pre-processing the received data in a conventional manner to reduce the data as well as to place or modify the data into a desired format. Reducing the data can include vertical or horizontal reduction. An embodiment of vertical reduction includes applying a reduction algorithm operable to remove data for parameters from consideration that is calculated to be not contributive to the calculation of utilization demand or the calculation of the mode of procurement. An embodiment of horizontal reduction includes aggregating data (e.g., averaging, selecting minimum value, selecting maximum value, etc.).

Act 260 includes analyzing the data of act 255 to calculate and display costs associated with current utilization of the assets 105, 110, and 115. Act 265 includes calculating a projected demand or utilization of the at least one asset 105, 110, and 115 dependent on a function of one or more of the measured parameters described herein. An embodiment of the act 265 includes calculating a trend or slope of the acquired or historical data for the measured utilization of the asset 105, 110, and 115 over a selected time interval. The act 265 can include executing a linear or non-linear regression analysis, a least squares analysis, or other conventional mathematical techniques to calculate a slope (e.g., assets per day) approximating the trend in the acquired data of the utilization of the selected asset 105, 110, and 115 over the selected time interval (e.g., 365 days, monthly). The act 265 can further include aggregating (e.g., minimum, maximum, average, sum, count, etc.) and/or normalizing the slope (e.g., to a value of one). The act 265 can further include multiplying the calculated slope with a selected projected time interval so as to calculate the projected demand or utilization of the asset 105, 110, 115 for the projected time interval. The calculated projected demand can be adjusted with one or more periodically upgraded factors for existing assets 105, 110 and 115 and one or more business direction factors. For example, the upgrade factor can be adjusted based on comparison of performance of existing to new assets 105, 110, and 115. The factors can also be representative of a predicted useful life of the asset 105, 110, 115. Values of the factors for the performance or useful life can be updated based on the acquired data from the assets 105, 110, and 115 over time, or can be predetermined and stored in the system 100.

An embodiment of the calculating act 265 of the projected demand looking forward in time can also be adjusted by a business adjustment factor representative of a business direction data as received in act 265. For example, the business adjustment factor can be calculated to reflect inputted user information for expansion or shrinkage of the facility, addition or removal of departments or services, local competition, etc. received via the user input device 165. The projected demand would then be calculated by multiplying the number of assets 105, 110, and 115, the normalized value of the calculated slope approximating the trend in demand, the upgrade factor, and the business adjustment factor. Act 265 can further include communicating the projected demand over the projected time interval for illustration or display at the output device 170. The projected or predicted demand or need can be expressed as an absolute number or it can be expressed as a mathematical distribution (e.g., normal, cyclic, eschewed, parabolic, etc.). An example of the projected demand can be for a projected rental demand of the selected asset 105, 110, and 115. An embodiment of act 265 can also include dependence on parameters for demographic changes of each department, growth of each department, etc., and adjusting the projected demand in accordance or in correlation to the value of the parameters. For example, act 265 can include calculating a patient increase factor (PIF) for each department of the entity, and multiplying the projected demand with the (PIF) to compute an adjusted projected demand.

For example, the acquired asset utilization data per day is used in an algorithm to calculate values of parameters in calculating a prediction of demand or need of a number of each type of asset 105, 110, and 115 in the entity at a future time. According to this example, daily asset utilization data acquired for a particular type of asset 105, 110, and 115 is aggregated to three days, five days, thirty days, and twelve months. The daily utilization, three-day utilization, five-day utilization, thirty-day utilization, and twelve-month utilization are implemented as parameters in the algorithm to predict a future need of the assets 105, 110, and 115. Other additional parameters implemented to predict future needs of assets 105, 110, and 115 include evolution parameters of the assets 105, 110, and 115, financial parameters, commercial parameters, entity growth parameters, etc. The above-described forecast or predicted demands or needs of each asset 105, 110, and 115 or asset type thereof is aggregated for illustration to the user.

Act 270 includes comparing the predicted or future need of each type of asset with the number of current assets 105, 110, and 115. An embodiment of act 270 includes calculating or comparing whether a rearrangement or movement of surplus of assets 105, 110, and 115 at certain location or department can meet the predicted demand at another location or department.

If it is calculated or identified that there is an insufficient number of one or types of assets 105, 110, and 115 to satisfy a predicted need or demand at a location or department as calculated in act 248, then act 255 includes calculating a mode (e.g., purchase, lease, rent, etc.) to procure or acquire assets 105, 110, and 115. An embodiment of act 275 includes calculating a predicted or projected cost for the projected demand of the asset 105, 110, and 115 for various modes of procurement. An embodiment of the act 275 can include comparing the projected costs for several alternatives manners of procurement to meet the projected demand. For example, the act 275 can include receiving a rental rate and at least one rental rule for the at least one asset, and multiplying a projected rental cost based on the rental rate and the projected rental demand for the selected time interval. The act 275 can also include receiving a purchase cost and a depreciation rate of the at least one asset 105, 110, and 115, and calculating a projected value of the least one asset 105, 110, and 115 equal including the purchase cost less the depreciation rate multiplied by the projected rental time interval. An embodiment of act 275 can also include communicating the at least one projected cost for each manner of procurement for illustration or display at the output device 170. An embodiment of act 275 can also include calculating a recommended number of assets of a particular type to be procured via a combination of purchasing, renting, or leasing in accordance to the calculated trend in utilization described above.

Act 275 can also include comparing the analyzed data calculated above for illustration to the user. An embodiment of the act 275 can include illustrating the projected purchase value of the least one asset 105, 110, and 115 in comparison to the rental cost for the projected rental time interval. Act 275 can also include comparing one or more of the calculated utilization, projected demand, and projected cost to other data acquired by other facilities (e.g., different healthcare networks, different hospitals, etc.) or clusters thereof of similar characteristics for comparison, the other data stored at the embodiment of the controller 150 that is in communication with a series of facilities or entities of different ownership or corporation.

An embodiment of act 275 can further include creating and executing a recurrent neural network classifier algorithm operable to generate the output of the best mode of procurement of assets 105, 110, and 115 for illustration to the operator. The classifier algorithm is configured to produce a binary output or result representative of a best mode of whether to procure the assets 105, 110, and 115 via purchase versus rent/lease. Parameters or factors incorporated in the classifier algorithm to calculate the best mode (e.g., purchase, lease, rent, etc.) to procure the assets 105, 110, and 115 includes price (purchase price versus rent/lease cost), parameter representative of an availability of the asset, buying a parameter representative of a favorability of terms of purchase in comparison to terms of rent/lease, parameter representative of a degree of change in product evolution versus current asset, a parameter representative of a business direction of the entity (e.g., expansion or contraction of budget), change in tax laws, change in inflation, etc. One embodiment of the recurrent neural classifier algorithm of act 255 is described in U.S. application Ser. No. 11/779,632 entitled "SYSTEM AND METHOD TO CALCULATE PROCUREMENT OF ASSETS", filed Jul. 18, 2007 and is hereby incorporated herein by reference in its entirety. The embodiment of the classifier algorithm employs a Recurrent Neural Network technique to calculate a best mode to procure the assets 105, 110, and 115. Yet, alternative fuzzy neural network techniques or a Back Propagation trained Multilayer Perception (MLP) technique can be used or in combination with the described recurrent neural classifier algorithm of act 275.

Act 380 generally includes displaying the mode or manner to procure the predicted need for the assets 105, 110, and 115 at the output device 170 to the user. Act 385 is the end of the method 200.

Figure 4B:
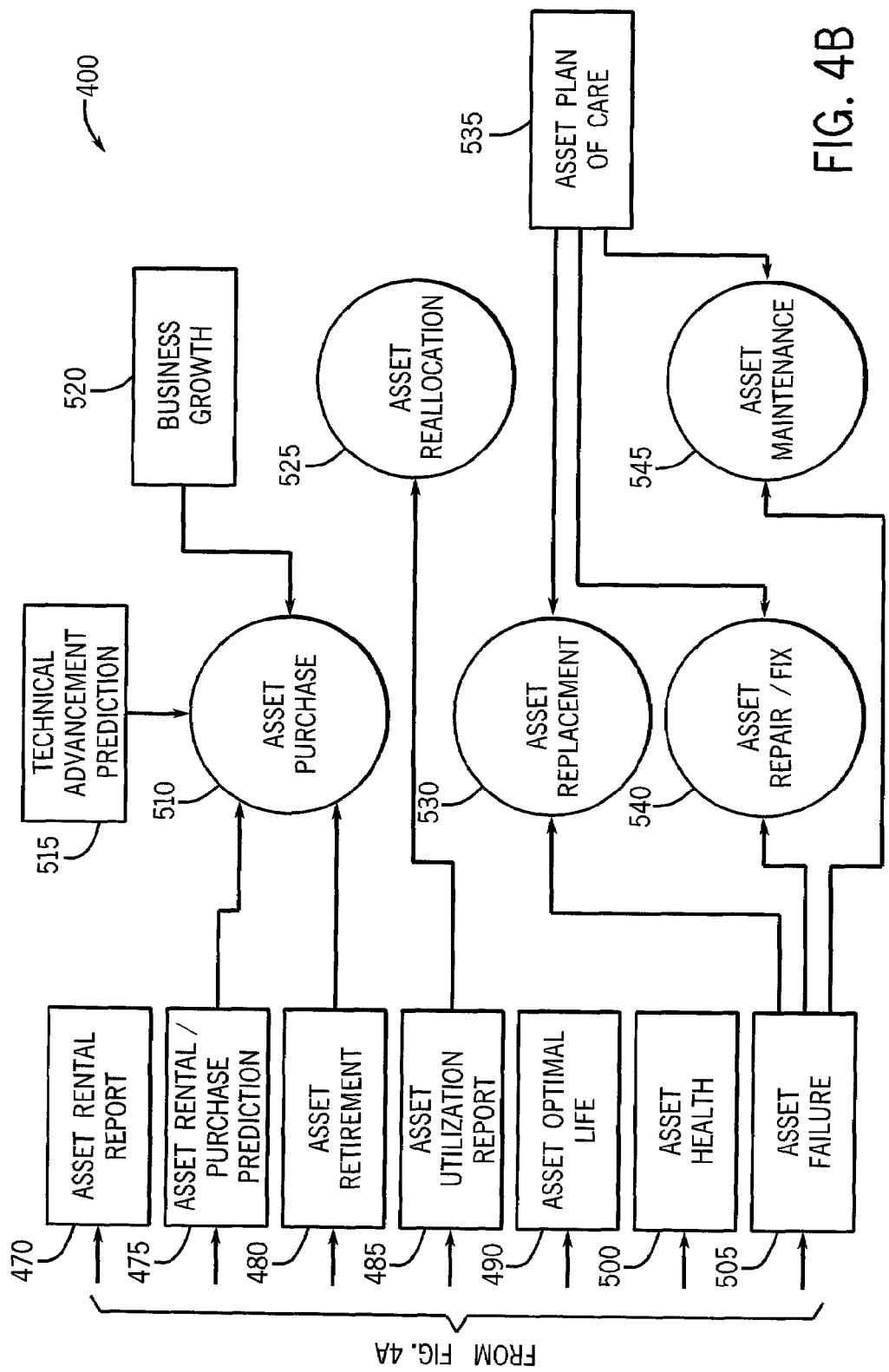

FIG. 4 illustrates an embodiment of a framework 400 of modules of computer-readable program instructions for execution by the system 100 to manage an end-to-end utilization and functionality of the series of assets 105, 110, 115, from planning to acquire the assets 105, 110, 115 to a retirement or disposal of the assets 105, 110, 115, as described above. The foregoing description of the framework 400 is directed to a healthcare environment or entity (e.g., hospital, clinic, etc.), yet the framework 400 can be directed to a manufacturing entity, a security entity (airport security), etc. and is not limiting on the subject matter described below.

A first module 405 of computer-readable program instructions is operable to request or receive input data of the utilization and location of the assets 105, 110, 115, similar to the acts 210 and 215 described above. An embodiment of the input data of the utilization and location of the assets includes tracking a location of each asset 105, 110, 115 or groups thereof, and tracking a current state or status of utilization (e.g., dirty, in use, in service, etc.). An embodiment of a second module 410 of computer-readable program instructions is generally operable to request or receive historical data (e.g., asset utilization, asset location, patient inflow, etc.) of the utilization data and location of the assets 105, 110, 115. An embodiment of a third module 415 of computer-readable program instructions is generally operable to request or request data of a segmentation or clustering of a series of independent entities 416, 417, 418 (e.g., hospitals, clinics, etc.) of similar services or that own or lease assets 105, 110, 115 of similar in function, type/category or construction. Clustering or segmentation generally refers to characteristics to group a series of entities 120, 416, 417, 418, such as types of services, patient capacity, infrastructure, etc.).

A fourth module 420 of computer-readable program instructions is generally operable to calculate a predicted trend in demand or need or utilization of the assets 105, 110, 115 for a future time period dependent on the data acquired from the first, second, and third modules 405, 410, 415 described above, similar to act 245. An embodiment of the fourth module 420 calculates and communicates a predicted demand for a type or a quantity of assets to a fifth module 425, a predicted utilization of the assets 105, 110, 115 to a sixth module 430, a predicted need for maintenance/service of the assets 105, 110, 115 to a seventh module 435, a predicted demand for a change in infrastructure (e.g., a communication infrastructure to a eighth module 440, a location infrastructure to an ninth module 445, a need for sensors or tools (for optimal operation/maintenance of the assets 105, 110, 115) to a tenth module 450, and a demand for a fleet of the assets 105, 110, 115 to a eleventh module 455) for each of the assets 105, 110, 115 of the entity 120, 416, 417, 418. Each of the above-described modules 420, 425, 430, 435, 440, 445, 450, 455 is operable to generate a report (e.g., display, printout, etc.) of the respective predicted demand or need of the assets 105, 110, 115 of the respective output described above for illustration at the output device 170.

An embodiment of an asset business analysis module 460 is generally operable to receive the predicted demand for maintenance/service, a predicted demand for the location of the assets 105, 110, 115, and the predicted demand for the type and number of the assets 105, 110, 115. Directed to the healthcare industry, an embodiment of the business analysis module 460 also includes storing data of business direction or expansion/contraction of services/maintenance in heterogeneous data sources integrated on a modality or department level (e.g., diagnostic, interventional, clinical, emergency, etc.). The data can be generally organized at the enterprise level to support end-to-end management of assets 105, 110, 115 from procurement to disposal.

Dependent on the above described received input data and generated output data of the asset business analysis module 460, an embodiment of module 470 is operable to generate a report of a tracked current amount and cost to rent one or more of the assets 105, 110, 115. An embodiment of the module 470 is generally operable to generate a rental report that can include a cost on a varying time basis (e.g., monthly or weekly basis) dependent on current or predicted duration (e.g., days, hours, or minutes) of utilization of the respective assets 105, 110, 115, and a summary of a vendor specification of mode and frequency of payment to a vendor.

An embodiment of module 475 is operable to generate a report of a cost and a prediction of rent versus purchase to meet the projected need or demand of the assets 105, 110, 115.

An embodiment of module 480 is operable to generate a report of a current and predicted retirement or disposal of assets 105, 110, 115. An embodiment of the module 480 includes computer readable program instructions operable to calculate/identify and to generate a report or display of the predicted need to retire or dispose of one or more of the assets 105, 110, 115. The module 480 includes a set of rules or algorithm to calculate whether the asset 105, 110, 115 should be retired/disposed of, and stored instructions of a procedure to retire/dispose of the asset 105, 110, 115. An embodiment of the module 480 includes one or more program instructions that calculate whether to retire/dispose of the asset 105, 110, 115 dependent on a number and duration time that the asset 105, 110, 115 is in service, a number of sufficient assets 105, 110, 115 of the same or similar function, and a measured parameter or factor generally indicative if sale is feasible or profitable, etc.

An embodiment of module 485 is operable to generate a report of a current and predicted utilization of each of the assets 105, 110, 115. An embodiment of the module 485 includes computer program instructions operable to operable to calculate and generate an output/report including: the duration of time that an asset 105, 110, 115 is used on any given day, the state or status of the assets at any given time, location of the asset 105, 110, 115 at any given time, a periodic utilization (e.g., daily, weekly, monthly, quarterly, yearly) of each individual or grouping of the assets 105, 110, 115, and a comparison of current utilization relative to past utilization recorded for same or similar historical time periods. The module 485 is also operable to calculate and generate an output indicative of a historical trend of utilization profile (e.g., duration of utilization, type and number of assets 105, 110, 115, duration of idle time when not being utilized, etc.). This historical trend can also be calculated or adjusted (e.g., business adjustment factors, infrastructure changes, expansion/contraction of services, etc.) to project or forecast a future need or demand of utilization of the assets 105, 110, 115, maintenance of the assets 105, 110, 115, or related functionalities. Asset idle time is generally a measure of a duration that the asset 105, 110, 115 is tracked to be in the inventory state or cleaning state.

An embodiment of module 488 is generally operable to analyze and generate a report illustrative of a health analysis of the system 100, including illustrations of received input data of the current and predicted demand of the type and amount of the assets 105, 110, 115, the utilization (e.g., fluctuation, duration, etc.) of the assets 105, 110, 115, and the type and number of tracking devices (e.g., sensors) to track the assets 105, 110, 115. An embodiment of the output of the module 488 includes one or more of: generating a report or display at the output device 170 of an expected life of the assets 105, 110, 115. An embodiment of a module 488 is also operable to generate a display at the output device 170 illustrative of a status or an availability (e.g., a health or working condition of the assets 105, 110, 115 or of a failure mode of the one or more assets 105, 110, 115) of each of the assets 105, 110, 115 relative to their tracked locations thereof. An embodiment of the display at the output device 170 can include a pictorial display of the locations (e.g., room reference, coordinates, etc.) of the assets 105, 110, 115 at the entity according to tracked data relative to a known layout of the entity, and a graphical illustration of the availability or utilization of the asset 105, 110, 115 (e.g., dirty, in use, inventory, cleaning, in service/maintenance, etc.). Alternatively, the location and availability of each asset 105, 110, 115 can be illustrated as a spreadsheet, including information of location and the state of utilization of the asset 105, 110, 115.

Dependent on received data from the module 488, module 490 is generally operable to generate a report or display of a current and predicted life of utilization of the assets 105, 110, 115.

Module 500 is generally operable to generate a report or display of a current status or state of the assets 105, 110, 115. An embodiment of module 500 is operable to manage and automatically predict asset health (e.g., predicted time to retirement or disposal of asset, predicted time to repair of asset, etc.), including a predicted date or time of failure or a predicted future date or time to retirement or disposal. Dependent on the predicted time frame or period to failure or retirement or disposal, the module 500 is operable to automatically generate a request or report to replace or repair the asset 105, 110, 115 according to the data of best mode of procurement described herein.

Module 505 is generally operable to generate a report or display of a current and predicted type and number of failures of the one or more assets 105, 110, 115.

The above-described received input to, and generated output of, the modules 460, 470, 475, 480, 485, 488, 490, 500, 505 can be aggregated on a generally daily-, weekly-, monthly- or yearly-basis or combination thereof.

An embodiment of module 510 is operable to receive the above-described output or reports from modules 475 and 480. The module 510 is also operable to receive a factor representative of a prediction of technical advancement of assets 105, 110, 115 (e.g., personnel) from module 515, and a factor representative of a predicted business growth from module 520. Dependent on the above-described data, the module 510 is generally operable to calculate the type, the predicted need or demand, and an amount, a type of, and the mode of procurement (e.g., purchase versus rental) of the assets 105, 110, 115.

An embodiment of the module 510 calculates an output that includes a future need or demand of each asset 105, 110, 115, correlated costs, a time of procurement (e.g., purchase or rental) of the assets 105, 110, 115, and a predicted vendor(s) dependent on factors including data of a current inventory and utilization of the assets 105, 110, 115, data of representative of business direction (e.g., factors representative of predicted expansion/contraction, predicted competition, predicted regulations, etc.), and technical data (e.g., useful life) of the assets 105, 110, 115. One embodiment of the module 510 receives input data of asset utilization, a factor or data of business direction, and technical data (e.g., useful life, maintenance costs, etc.) of the assets 105, 110, 115. The input data is integrated, cleaned and pre-processed to enhance data reduction and data consistency (e.g., both format as well as content wise). The cleaned data is communicated for implementation in an algorithm to calculate the predicted need or demand, correlated costs, recommended timing of acquisition, and predicted vendor to acquire or procure the assets 105, 110, 115.

Module 525 is generally operable to assign or reallocate assignment of the assets 105, 110, 115 among a series of different departments or locations according to tracked or predicted demand or need of the assets 105, 110, 115 as described herein. An embodiment of the module 525 is operable to calculate utilization of the assets 105, 110, 115 and duration thereof, and compare relative to a predetermined capacity value. Thereby, the module 525 is operable to calculate or locate current and predicted surpluses or shortages of assets 105, 110, 115 on a department level of a hospital entity, and identify re-location of assets to meet or most nearly meet predicted needs or demands, or to achieve a more balanced distribution of assets 105, 110, 115.

Module 530 is generally operable to calculate and generate a report illustrative of a useful life, cost of repair and maintenance, and a recommendation whether to replace each asset 105, 110, 115. An embodiment of the module 530 calculates and generates the recommendation whether to replace the asset 105, 110, 115 dependent on received input data of a tracked level of functioning, cost and time of repair/maintenance, availability of better technology of better productivity, an indication or report of a failure of the asset 105, 110, 115, a received plan of care of the asset 105, 110, 115. The module 530 compares the input data relative to predetermined levels or values, or enters the above data into an algorithm to calculate a recommendation whether to replace. According to one example, the module 530 calculates and generates a report to replace any of the assets 105, 110, 115 if a cost of replacement of any asset 105, 110, 115 is less than a cost of operation of the asset 105, 110, 115, if a cost of replacement is less than a cost of maintenance or repair, or if the asset 105, 110, 115 has reached an end of useful life according to stored data of predicted life.

Module 540 is generally operable to identify and communicate a report illustrative of assets in need of repair or to be fixed. One embodiment of the module 540 identifies assets 105, 110, 115 in need of repair or to be fixed dependent on input of partial or total non-functioning (e.g., number of failures, need to calibrate, etc.) of the asset 105, 110, 115 in comparison to a predetermined level. Dependent on tracking partial or total non-functioning of the asset 105, 110, 115, the module 540 calculates a prediction of a failure of the asset 105, 110, 115 before actual failure of the asset 105, 110, 115, a window of time that asset 105, 110, 115 is predicted to fail, a predicted need of parts and personnel/technician to repair the failure of the asset 105, 110, 115, and a predicted schedule to repair the asset 105, 110, 115.

Module 545 is generally operable to track and identify demand or need of maintenance of each of the assets 105, 110, 115. An embodiment of module 545 receives input of the location, tracked utilization, and tracked service life of the assets 105, 110, 115. Dependent on this input data, the module 545 is operable to identify and generate a report illustrative of assets 105, 110, 115 in need of maintenance, and calculate and report a priority to scheduling maintenance of the assets 105, 110, 115 relative to one another. For example, certain assets 105, 110, 115 may need to be serviced at fixed interval due to a regulatory requirement, whereas other certain assets 105, 110, 115 get overused, or the assets 105, 110, 115 are underused and not in immediate need of servicing at the same interval relative to the other assets 105, 110, 115. The module 545 calculates the servicing need and costs dependent on the above data to calculate a schedule of needed maintenance that enhances return on investment from each asset 105, 110, 115.

The above-described illustrations of the modules 405, 410, 415, 420, 425, 430, 435, 440, 445, 450, 455, 460, 465, 470, 475, 480, 485, 490, 500, 505, 510, 515, 520, 525, 530, 535, 540, 545 that comprise the framework 400 in FIG. 4 can be a dashboard 560 of graphic icons (represented by reference to modules 405, 410, 415, 420, 425, 430, 435, 440, 445, 450, 455, 460, 465, 470, 475, 480, 485, 490, 500, 505, 510, 515, 520, 525, 530, 535, 540, 545) for illustration in a display 170, where the icons are interactive such that selection via an input device 165 (e.g., touch-screen, mouse device) can trigger or cause display of tracked or calculated data as described herein directed to the respective modules 405, 410, 415, 420, 425, 430, 435, 440, 445, 450, 455, 460, 465, 470, 475, 480, 485, 490, 500, 505, 510, 515, 520, 525, 530, 535, 540, 545. A technical effect of the dashboard 560 shown in FIG. 4 is to provide a tool to track and manage the assets 105, 110, and 115 from procurement to an end of useful life (e.g., retirement, disposal, replacement, etc.), as well as to provide a tool to predict procurement of assets directed to a future time period or date.

Figure 5:
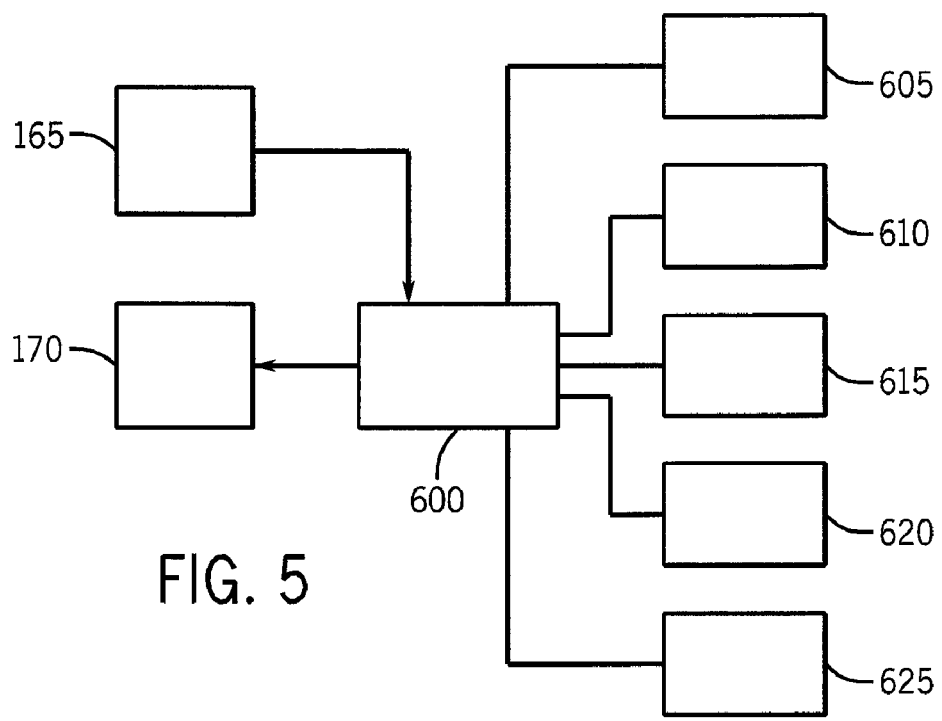
FIG. 5 shows a schematic diagram of an embodiment of system to cluster a series of entities in accordance to the framework of FIG. 4.

Referring to FIG. 5, the system 100 also includes module 600 of computer readable program instructions operable to cluster or segment a series of entities 605, 610, 615, 620, 625 dependent on a comparison of similarities or differences to one another in a peer organization, similar to that described of the module 415 in FIG. 4. One goal of clustering entities 605, 610, 615, 620, 625 into similar groups (clusters) is to determine those close or similar to one other with respect to one or more clustering factors (intrinsic grouping). The factors can be include tracked type and amount of utilization of assets 105, 110, 115, repair/troubleshooting history of those entities 605, 610, 615, 620, 625, dispatch information, procedure performed by the entities 605, 610, 615, 620, 625, any of the measured parameters or calculations described above with respect to the framework 400, and so on. The benefit of clustering of hospitals includes but not limited to encouraging competition, optimal utilization of assets 105, 110, 115, the development of operational efficiencies including the rental cost versus purchase cost of the assets 105, 110, 115.

An embodiment of clustering herein refers to detecting or calculating similar structure or characteristic parameters in a collection of unlabelled data (in our case the collection of entities 605, 610, 615, 620, 625). For example, one type of clustering of the entities 605, 610, 615, 620, 625 may include general service hospitals, while a second cluster may include clinics (e.g., urgent care), while another may include childrens hospitals, while yet others may include educational hospitals.

An embodiment of the clustering module 600 includes program instructions representative of a clustering algorithm operable to cluster or segment the series of entities 605, 610, 615, 620, 625 dependent on values of one or more parameters of the group comprising: types and number of assets 105, 110, 115, current and predicted types or needs of utilization of assets 105, 110, 115, type of business or services offered, tracked and predicted health of assets 105, 110 115, re-allocation of assets 105, 110, 115, predicted type or amount or cost or mode of procurement of assets 105, 110, 115, current and predicted replacement of assets 105, 110 115, current and predicted duration or frequency of repair of assets 105, 110, 115, or current or predicted duration or cost of maintenance of the assets 105, 110, 115, types of service (e.g., medical procedures performed), or any of the parameters or calculations described above with respect to the framework 400.

Figure 6:
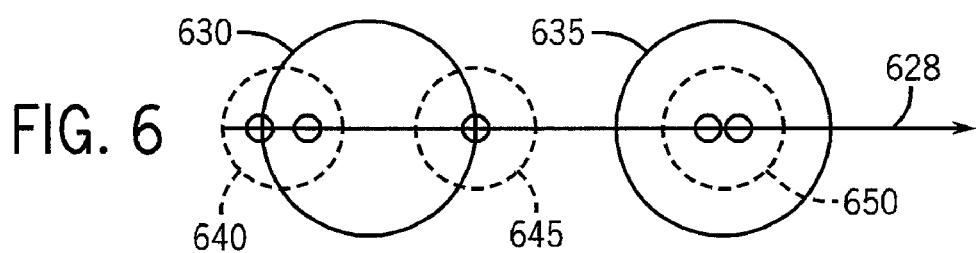
FIG. 6 illustrates a schematic diagram of an embodiment of an algorithm to cluster the series of entities of FIG. 5.

Referring now to FIG. 6, one embodiment of a clustering algorithm to identify cluster or groups or segments that comprise a series of entities 605, 610, 615, 620, 625 is herein referred to as exclusive clustering algorithm. Assume each of the series of entities 605, 610, 615, 620, 625 represents a data point arranged in value along an axis 628 as illustrated in FIG. 6. The exclusive clustering algorithm generally includes calculating a spatial relationship of values of a set of data points of a measured parameter of each of the independent entities 605, 610, 615, 620, 625; and assigning each data point of the set to a nearest centroid 630 and 635. The algorithm further includes re-calculating the centroids of each cluster of data points, and reassigning each of the data points to the newly calculated centroids 640, 645, 650. The algorithm terminates when no new centroids are calculated (i.e., the centroids do not move in the next iteration). This algorithm can be represented as the following mathematical function, also referred to as a sum of square error, as follows:

$$J = \sum_{j=1}^{K} \sum_{n \in Sj} |x_n - \mu_j|^2$$

where $(x_n)$ represents nth data point vector representative of one of the measured parameters described herein (e.g., utilization of asset, health of asset, maintenance of asset, etc.), and $(\mu_j)$ represents a geometric centroid of a cluster (Sj) of data points. It should be understood that one or a combination of clustering algorithms described herein can be employed to cluster or segment entities.

Another embodiment of the clustering algorithm to identify cluster or groups or segments of the series of entities is herein referred to as overlapping clustering algorithm. Assume each of the series of entities represents a data point. Execution of the overlapping clustering algorithm generally allows each of the series of entities or data points to belong to more than one cluster with varying degrees. For example, implementation of the overlapping clustering algorithm may calculate that the entity (e.g., a hospital) belongs to a first cluster with 98% membership and a second cluster with 2% membership. In this example, the entity can for practical purposes be considered to belong the first cluster. The overlapping clustering algorithm allows the identified clusters of a data points to switch or even be nondeterministic. For example, one of the clustering sets of data points can be referred to as "not sure" group generally representative that the algorithm is non-determinative in identifying or clustering the data points in this set.

The overlapping clustering algorithm can be represented at the following mathematical function:

$$J_m = \sum_{i=1}^{N} \sum_{j=1}^{C} u_{ij}^m \|x_i - c_j\|^2$$

where (m) is any real number greater than 1, $(u_{ij})$ is the degree of membership of $(x_i)$ in the cluster (j), where $(x_i)$ is the ith measured data point, $(c_j)$ is a center of the cluster of data points, and $\|*\|$ is any norm expressing a similarity between any measured data and the center $(c_j)$. The algorithm includes iterating through the above mathematical function, and updating membership $(u_{ij})$ of the clusters of data points and the cluster centers $(c_j)$. Reiterating through the algorithm can end dependent on a termination criterion ($\epsilon$) (e.g., between 0 and 1).

Another embodiment of the overlapping algorithm assumes that each sample $(X_i)$ includes a graded or weighted (e.g., probability) or "fuzzy" membership of the entities 605, 610, 615, 620, 625 in at least one cluster. Probability (P) of membership in a cluster for each point can be normalized. Directed to a domain of healthcare related clusters of entities 605, 610, 615, 620, 625, the overlapping clustering algorithm allows a particular entity 605, 610, 615, 620, or 625 to be assigned or identified part of multiple clusters of entities 605, 610, 615, 620, 625.

For example, assume individual data points representative of entities 605, 610, 615, 620, 625 can be bound to each cluster by means of a membership function, which represents the "fuzzy" behavior of this overlapping cluster algorithm. The overlapping cluster algorithm includes a creating a matrix with factors of value between 0 and 1 to represent a degree of membership between data and centers of clusters of the entities 605, 610, 615, 620, 625. Instead of portions of the datum belong exclusively to a well-defined cluster, a membership matrix (U) generally represents that every datum may belong to several clusters with different values of the membership coefficient ranging in value between 0 and 1. For example, a value 0.2 of 'm' can indicate the degree of membership a cluster of entities 605, 610, 615, 620, 625 to each datum. The number of rows and columns depends on number of data points and number of clusters. A row (i) can represent a number of data points and a column (j) can represent a number of clusters, such that each element of the matrix can be denoted as U(i,j).

Figure 7:
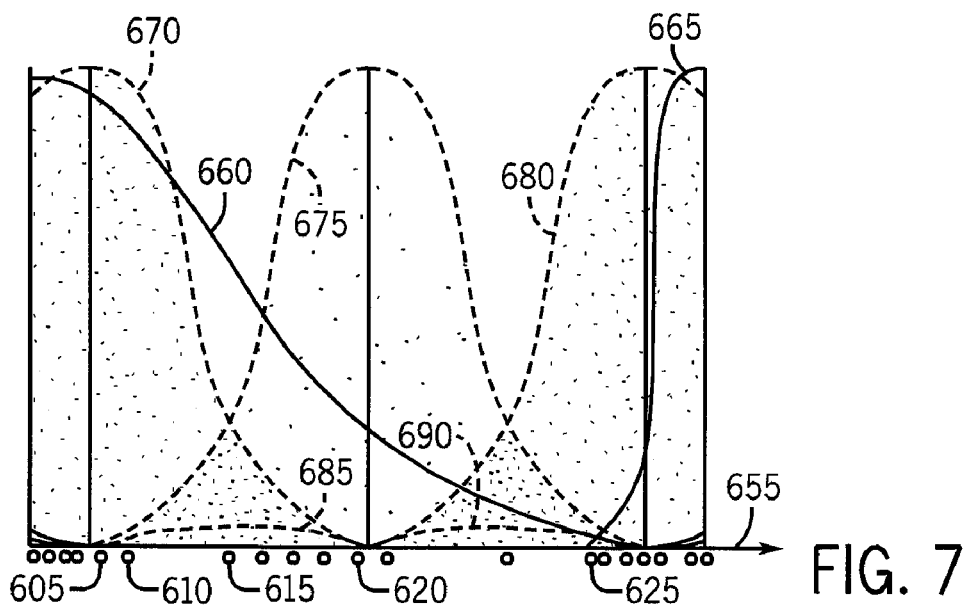
FIG. 7 illustrates a schematic diagram of another diagram of an algorithm to cluster the series of entities of FIG. 5.

FIG. 7 illustrates a schematic diagram of a mono-dimensional example of applying the overlapping algorithm to the set of entities 605, 610, 615, 620, 625 represented as data points distributed in value relative to an axis 655. The initial condition illustrates that the clustering or segmenting data points into two clusters (illustrated in solid line and reference 660 and 665) dependent on membership value of each data point relative thereto. Iterations of the algorithm can result in clustering of the entities 605, 610, 615, 620, 625 or data points five clusters (as illustrated in dashed line and reference 670, 675, 680, 685, 690).

Another embodiment of the clustering algorithm to identify groups or segments of the series of entities 605, 610, 615, 620, 625 is herein referred to as a hierarchical clustering algorithm. Implementing the hierarchal clustering algorithm includes assigning or identifying each item or entity to its own cluster (e.g., N items data set will have N clusters and an inter-item distance is the same as an inter-cluster distance), and iteratively merging entities identified or calculated to be closest (most similar in comparison of identified parameters) pair of clusters relative to others. The algorithm includes repeating the above-described iterations of identifying, calculating, and merging similar clusters of entities 605, 610, 615, 620, 625. Examples of one or more parameters under comparison include types of services offered, capacity, billing, number of assets, types of assets, etc.).

Another embodiment of the clustering algorithm is herein referred to as a divisive hierarchical algorithm, and is a variation of the above-described hierarchal algorithm. The divisive hierarchical algorithm includes initially assuming that all the data elements or entities 605, 610, 615, 620, 625 belong to one or a single cluster, and iteratively subdividing each cluster into smaller clusters of elements or entities 605, 610, 615, 620, 625 according to calculated differences in tracked parameters (e.g., types of services offered, capacity, billing, number of assets, types of assets, etc.) of the entities relative to one another.

Another embodiment of the clustering algorithm is herein referred to as probalistic clustering algorithm. The probalistic clustering algorithm generally includes executing probabilistic approaches to identify clusters or segments in a series of entities 605, 610, 615, 620, 625. An embodiment of the probalistic clustering algorithm is a model-based approach calculating a best-fit of a pre-defined clustering mathematical model relative to the acquired data. Assume that each cluster of entities 605, 610, 615, 620, 625 can be mathematically represented by a parametric distribution (e.g., Gaussian (continuous) or Poisson (discrete) distribution or combination thereof).

It should be understood that the number and types of clusters can vary according to practicality and differences between clusters or segments. A measure of a quality of the created clusters can be classified into internal (e.g., square-loss, log-likelihood, graph-cut value, etc.) and external quality measures (e.g., normalized mutual information, a supervised F-measure).

One embodiment of the module 600 is also operable to measure of a quality of the clustering by executing a statistical test to determine a homogeneity of the population. The process starts with the computation of mean vector and covariance matrix of the whole sample. The pseudorandom samples are drawn from each of the clusters, calculating a spread of clusters, and generating a sampling distribution of the spread. If a spread of the sample is among the highest, then the clusters are statistically significant. Another embodiment of a technique to measure quality of the clustering includes splitting samples between training and test cases (e.g., 70% training and 30% test), and comparing the cluster of the centroids of the sampled clusters of training cases relative to the cluster of the centroids of the test cases.

Examples of factors or parameters to cluster or group or segment one or more of the series of entities 605, 610, 615, 620, 625 includes the number and complexity of procedures performed, membership in a directory or other organization (e.g., the American Hospital Directory), a medical service index, similar inpatient percentage (frequency), under similar government regulations, similar competitive activities, or similar types or number of assets, similar ownership versus rental of assets relative to other entities 605, 610, 615, 620, 625. A technical effect of clustering into peer groups enables hospitals to analyze assets 105, 110, 115 from procurement to retirement/disposal (e.g., asset forecasting, asset procurement, asset allocation/reallocation, asset depreciation and others) even they do not have their own tracked data of utilization or other measured parameters described herein. The peer group data can be used in such cases.

Figure 8:
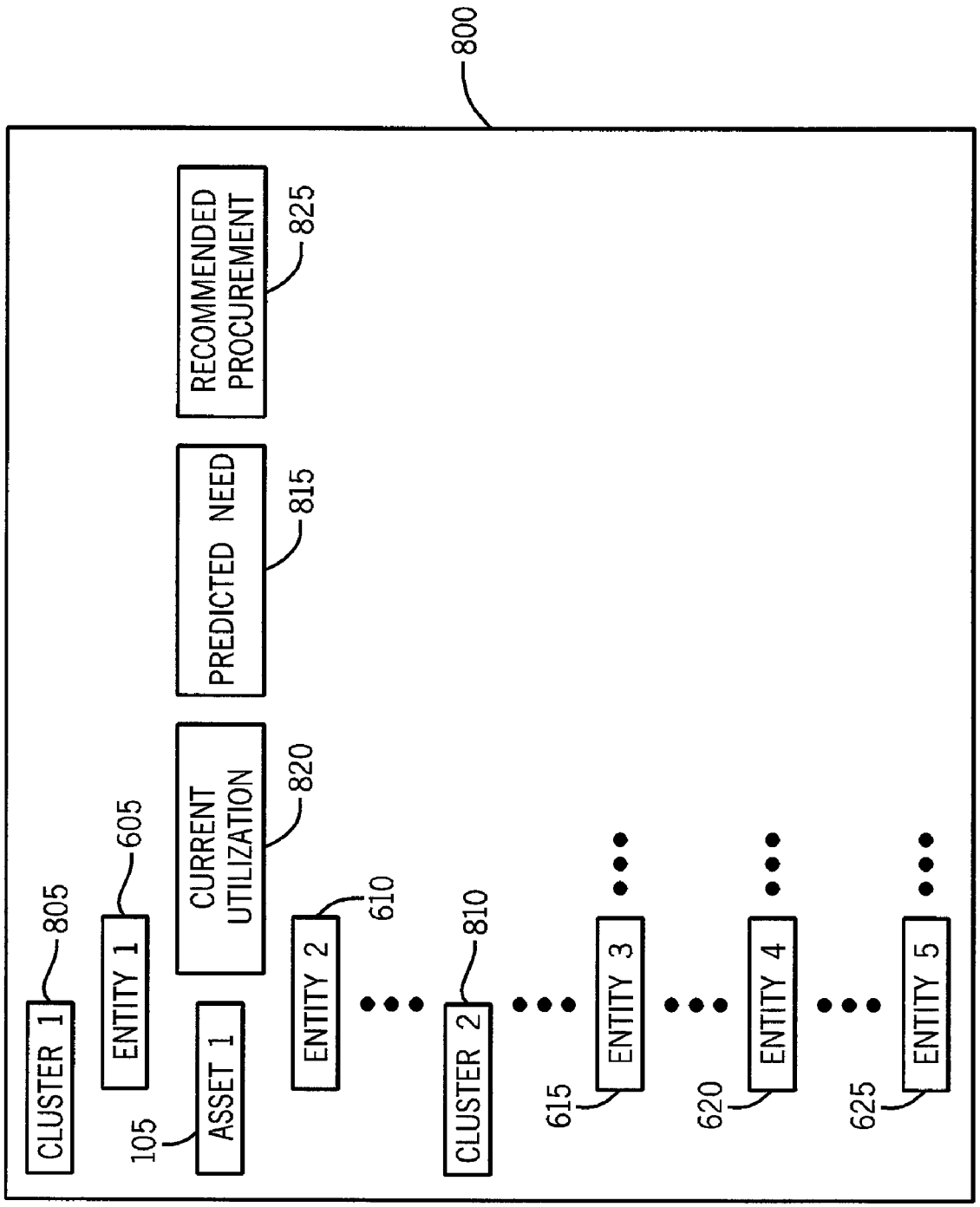
FIG. 8 illustrates an embodiment of a report illustrative of a comparison of clustering of a series of independent entities of FIG. 5.

Referring now to FIG. 8, after having calculated clusters or segments of the series of entities 605, 610, 615, 620, 625, the module 600 is also operable to generate a report or display 800 for illustration at the output device 170 (see FIG. 1). The illustrated embodiment of the report 800 includes representations 805, 810 illustrative of the segmenting of the series of entities 605, 610, 615, 620, 625 into a series of clusters. Of course, the number of the representations of the clusters 805, 810 can vary. The report 800 can further include an illustration 815 of a comparison of current or predicted needs, respectively, of one or more of the assets 105, 110, 115, an illustration 820 of a degree of utilization or duration of utilization of assets 105, 110, 115, and an illustration 825 of a predicted procurement of new assets 105, 110, 115 or a proposed or predicted relocation of current assets 105, 110, 115. Of course, the report 800 can include other an illustration of a predicted business direction, current infrastructure, cost and duration of maintenance of assets 105, 110, 115 (e.g., cleaning, sanitization, repair, calibration), or any other calculation or parameter described above. The system 100 may communication the report 800 from a central or back-office locations to remote or local computers or displays for illustration to the user.

An embodiment of the system 100 can also include computer readable program instructions to execute a calculation of a statistical relevance of acquired data each of the above-described parameters to enhance generation of recommendations of predicted needs and procurement to the user. An embodiment of the calculation of the relevance of acquired data can include a calculation of the entropy of the acquired data over time. This relevance analysis enhances ranking and filtering relevant from irrelevant data that may otherwise skew recommendations to enhance utilization, prediction of utilization, procurement of assets, etc.

It should be understood that any of the embodiments of the modules of computer readable program instructions described above can also operable to create or generate interface tools at the display 170 so as to receive input or requests to forecast, report, or receive queries. Also, each of the above-described embodiments of the modules can include instructions store data in the structured database or memory 160 (including a heterogeneous collection of data bases) or data in unstructured format (including flat files). Certain categories of the data can be extracted and pre-processed or transformed to remove any inconsistencies resulting in data in a standard format ready for further processing. The instructions can be to horizontally or vertically reduce the data to reduce the cost of computation while preserving the clustering to an acceptable range. The instructions may further include initially loading data, and then refreshing the data at a regular interval (e.g., daily), and to segment the data to enhance abstraction.

A technical effect of the system 100 and method 200 and framework 400 described above provides a tool to manage or predict asset health (e.g., predicted time to retirement or disposal of asset, predicted time to repair of asset, etc.). The system 100 and method 200 are operable to generate comparisons and reports illustrative of historical, current or predicted asset utilization, the future business direction, retirement/disposal of assets, predictive forecast of asset needs, recommendation of procurement for comparison via clustering/segmentation to similar entities or peers (e.g., clusters of hospitals) so as to enhance quality of service and reduce costs. The system 100 and method 200 is generally operable to generate reports or display 170 automatically as soon as new or relevant data is received, enhance the ability to mine acquired data, to support an ability to refresh data at a rate suitable for this type of applications, to adapt to or organize around varying subjects (e.g., as assets, patients, etc.), and to enhance a limit on decision-making analysis to relevant data, to integrate data from multiple heterogeneous sources (e.g., relational databases, hierarchical databases, flat files, transactional records, etc.), and to clean and integrate data to a common format, and be dynamic or time-variant.

Additional technical effects of the above-described system 100 and method 200 and framework 400 described above further include providing a tool to enhance management decisions to predict needs/demands and mode to procure (e.g., purchase versus rent/lease) assets 105, 110, 115 by an entity 120, 416, 417, 418 (e.g., a hospital). The system 100 and method 200 and framework 400 are operable to receive input data so as to calculate trends in the utilization (fluctuations, duration, etc.) of the assets 105, 110, 115, the cost of maintenance (impacting buy as well as lease), rental charges, useful life of the asset 105, 110, 115, etc. and then employ this data to calculate or identify a recommendation of predicted demands and mode of procurement.

This written description uses examples to disclose the subject matter, including the best mode, and also to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method to manage utilization of a plurality of types of assets having at least one tracking element by a plurality of independent entities, the method comprising the steps of:

using a tracking system including a controller having a processor to detect a measure of time of one or more of the plurality of assets at a location, wherein the tracking system communicates with the plurality of assets through the at least one tracking element;

via the controller, determining, based on a location detected by the tracking system, a status of the one or more of the plurality of assets, wherein the statuses include CLEANING, SERVICE, INVENTORY, USE, and DIRTY;

receiving a plurality of parameters of utilization from each of the plurality of independent entities, wherein at least one of the plurality of parameters of utilization comprise the measure of time in one or more of the statuses;

segmenting the plurality of independent entities into more than one cluster dependent on identified similarities in at least one of the plurality of parameters of utilization of the one or more of the plurality of entities, wherein the step of segmenting includes calculating a relationship of a set of data points of at least one measured parameter of each independent entity relative to a reference, assigning each data point of the set to a nearest centroid; and assigning each of the centroids as one of the clusters; and generating a display of a comparison of the plurality of parameters of utilization of each of the independent entities relative to another in each of the plurality of clusters.

2. The method of claim 1, wherein each of the independent entities in a first cluster includes a parameter of value within a predetermined threshold of time of utilization of an asset of at least a similar function in delivering healthcare.

3. The method of claim 1, wherein the plurality of parameters of utilization includes one or more of the group comprising: a historical data of tracked duration of utilization of each of the plurality of types of assets, and a tracked data of disposal of each of the plurality of types of assets.

4. The method of claim 1, wherein the plurality of parameters of utilization includes a predicted trend in mode of procurement of additional assets of each of the plurality of types of assets.

5. The method of claim 1, wherein the step of segmenting includes measuring a plurality of data points of a common parameter of each of the plurality of independent entities; creating a matrix comprising a plurality of factors generally representative of a degree of similarity of each data point to each of the clusters.

6. The method of claim 1, wherein the step of segmenting includes one of: iteratively combining a pair or more of clusters dependent on a calculated similarity in value of a common parameter, and iteratively subdividing one or more of the plurality clusters into a pair or more of smaller clusters according to a calculated difference in tracked parameters.

7. The method of claim 1, wherein the step of segmenting includes a probability of each of the plurality of entities to fit in one of the pluralities of clusters dependent on a tracked parameter, and wherein each of the cluster of entities can be represented as a parametric distribution.

8. The method of claim 1, wherein the step of segmenting the plurality of independent entities into clusters is dependent on one of the following group of utilization parameters comprising: a membership in a directory, assignment in a medical service index, a tracked percentage of inpatient procedures, under a one or more common government regulations, and a percentage of ownership versus rental of assets.

9. A system to manage utilization of a plurality of types of assets having a tracking element by a plurality of independent entities, comprising:

a tracking system configured to detect a measure of time of one or more of the plurality of assets at a location, the tracking system being configured to communicate with the plurality of assets through the at least one tracking element, the tracking system comprising:

a controller including a processor operable to execute a plurality of program instructions stored in a memory, the plurality of program instructions generally representative of the steps of:

determining, based on a location detected by the tracking system, a status of the one or more of the plurality of assets, wherein the statuses include CLEANING, SERVICE, INVENTORY, USE, and DIRTY;

receiving a plurality of utilization parameters from each of the plurality of independent entities, wherein at least one of the plurality of parameters of utilization comprises the measure of time in one or more statuses;

segmenting the plurality the independent entities into more than one cluster dependent on identified similarities in at least one of the plurality of utilization parameters of the one or more of the plurality of entities, wherein the step of segmenting includes calculating a relationship of a set of data points of at least one measured parameter of each independent entity relative to a reference, assigning each data point of the set to a nearest centroid; and assigning each of the centroids as one of the clusters; and generating a display of a comparison of the plurality of utilization parameters of each of the independent entities relative to another in each of the plurality of clusters.

10. The system of claim 9, wherein each of the independent entities in a first cluster performs at least one service in common with one another.

11. The system of claim 9, wherein the plurality of utilization parameters includes one or more of the group comprising: a historical data of tracked duration of utilization of each of the plurality of types of assets, and a tracked data of disposal of each of the plurality of types of assets.

12. The system of claim 9, wherein the plurality of utilization parameters includes a predicted trend in mode of procurement of additional assets of each of the plurality of types of assets.

13. The system of claim 9, wherein the step of segmenting includes measuring a plurality of data points of a common parameter of each of the plurality of independent entities; creating a matrix comprising a plurality of factors generally representative of a degree of similarity of each data point to each of the clusters.

14. The system of claim 9, wherein the step of segmenting includes one of: iteratively combining a pair or more of clusters dependent on a calculated similarity in value of a common parameter, and iteratively subdividing one or more of the plurality clusters into a pair or more of smaller clusters according to a calculated difference in tracked parameters.

15. The system of claim 9, wherein the step of segmenting includes a probability of each of the plurality of entities to fit in one of the pluralities of clusters dependent on a tracked utilization parameter, and wherein each of the cluster of entities can be represented as a parametric distribution.

16. The system of claim 9, wherein the step of segmenting the plurality of independent entities into clusters is dependent on one of the following group of utilization parameters comprising: a membership in a directory, assignment in a medical service index, a tracked percentage of inpatient procedures, under a one or more common government regulations, and a percentage of ownership versus rental of assets.

17. The method of claim 1, comprising calculating a trend in utilization of at least one of the one or more of the plurality of assets based on dwell time of the assets of the at least one plurality of assets in the USE state.

18. The method of claim 17, comprising calculating projected demand for the at least one plurality of assets based on the calculated trend and at least one of: an upgrade factor based on a comparison of existing assets of the at least one plurality of assets to new assets, or a business adjustment factor representative of user input on future business conditions.

* * * * *